United States Patent [19]
Brul et al.

[11] Patent Number: 5,888,504
[45] Date of Patent: Mar. 30, 1999

[54] NATURAL COMPOSITION FOR COMBATTING FUNGI

[75] Inventors: Stanley Brul, Vlaardingen, Netherlands; Peter Coote, Sharnbrook, United Kingdom; Shanti Dielbanhoesing, Vlaardingen, Netherlands; Suzanna Oomes, Vlaardingen, Netherlands; Wilma M. Stam, Vlaardingen, Netherlands; Geke Naaktgeboren-Stoffels, Vlaardingen, Netherlands; Malcolm Stratford, Sharnbrook, United Kingdom

[73] Assignee: Van den Bergh Foods Co., Division of Conopco, Inc., Lisle, Ill.

[21] Appl. No.: 742,730

[22] Filed: Nov. 1, 1996

[30] Foreign Application Priority Data

| Nov. 3, 1995 | [EP] | European Pat. Off. | 95202977 |
| Nov. 3, 1995 | [EP] | European Pat. Off. | 95202978 |
| Nov. 3, 1995 | [EP] | European Pat. Off. | 95202979 |

[51] Int. Cl.⁶ .......................... A61K 38/43; A61K 38/47; A61K 38/54; A23L 3/3463
[52] U.S. Cl. ............ 424/94.1; 424/94.2; 424/94.6; 424/94.61; 424/94.62; 424/63; 424/70.1; 426/61; 426/532
[58] Field of Search .................. 424/94.1, 94.2, 424/94.5, 94.6, 94.61, 94.62, 63, 70.1; 426/532, 61

[56] References Cited

U.S. PATENT DOCUMENTS

| 5,173,419 | 12/1992 | Harman et al. | 435/209 |
| 5,486,503 | 1/1996 | Oppenheim et al. | 514/2 |
| 5,631,228 | 5/1997 | Oppenheim et al. | 514/12 |

FOREIGN PATENT DOCUMENTS

| 427912 | 5/1991 | European Pat. Off. . |
| 448511 | 9/1991 | European Pat. Off. . |
| 466244 | 1/1992 | European Pat. Off. ...... A23L 3/3571 |
| 90/03732 | 4/1990 | WIPO . |
| 92/17591 | 10/1992 | WIPO .............................. C12N 15/56 |
| 94/12150 | 6/1994 | WIPO . |
| 96/06532 | 3/1996 | WIPO . |

OTHER PUBLICATIONS

Caccioni, D. et al. J. Essent. Oil Res., vol. 6, No. 2, pp. 173–179; Chemical Abstracts vol. 121, abstract No. 153119 (Abstract only), 1994.
Gould, G.W. Journal of Food Protection (supplement), pp. 82–86 (Abstract only), 1996.
European Search Report dated Apr. 2, 1996.
Patent Cooperation Treaty Report dated Feb. 27, 1997.
Derwent Abstract AN 82–90986E.
Derwent Abstract JP 57/022,681.
Derwent Abstract SU 39/4485.
Microbiology (1994) 140, 623–629 Lorito et al.
Int. Journal of Food Microbiology 24 (1995) 343–362 Holzapfel et al.

*Primary Examiner*—Mary E. Mosher
*Attorney, Agent, or Firm*—Matthew Boxer

[57] ABSTRACT

Composition suitable for combatting fungi characterized in that it comprises at least one fungi cell wall lytic enzyme and a natural microbial cell membrane affecting substance in an effective concentration. Preferably the composition is a food product.

8 Claims, 6 Drawing Sheets

(xi) SEQUENCE DESCRIPTION: SEQ ID NO: 1:

Phe Ala Ser Leu Leu Gly Lys Ala Leu Lys Ala Leu Ala Lys Gln
1               5                   10                  15

SEQUENCE LISTING ( 1 ) GENERAL INFORMATION:

( i i i ) NUMBER OF SEQUENCES: 1

( 2 ) INFORMATION FOR SEQ ID NO: 1:

( i ) SEQUENCE CHARACTERISTICS:
( A ) LENGTH: 15 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO: 1:

Phe Ala Ser Leu Leu Gly Lys Ala Leu Lys Ala Leu Ala Lys Gln
1               5                   10                  15

NATURAL COMPOSITION FOR COMBATTING FUNGI

The present invention is concerned with combatting fungi, particularly with the preservation of food against deterioration by fungal growth. Each year millions of tons of food are lost because of microbial spoilage. Man has discovered very early in history that fermentation with beneficial micro-organisms can contribute to the preservation of food. In the absence of modern refrigeration facilities inhabitants of tropical and subtropical regions still rely largely on fermentation as a means of preserving and safeguarding their food.

STATE OF THE ART

The micro-organisms which cause food spoilage comprise bacteria and fungi. Fungi present a spoilage hazard in food manufacturing. Low-fat spreads, cheese, tea-based beverages, fruit- and tomato-based products are vulnerable food products. An inactivating heat treatment is not always desirable or possible. Furthermore fungal spores present in factory halls can cause problems at the packaging stage. Combatting bacteria is relatively easy. Fungi, however, are organisms which can survive under very adverse conditions. Effectively combatting fungi by germination or growth inhibition is difficult, particularly when one wishes the use of natural preservatives only. Fungi inhibition is understood to comprise both killing the fungi and suppressing their growth without actually killing them.

Although for combatting fungi food technology has developed artificial, chemical preservation agents, an increasing number of consumers prefer food with ingredients which are not chemical, but have a natural origin. Therefore increasing attention has been given to find preservation agents which can be obtained by a fermentation process which is considered a natural preparation. Such agents comprise microbial cell wall lytic enzymes, which are described in e.g. the review paper "Biological preservation of foods with reference to protective cultures, bacteriocins and food-grade enzymes", Int. Journal of Food Microbiology, 24 (1995) 343–362. According to WO 90/03732 plants can be protected against fungi by treating them with fungal cell wall lytic enzymes, particularly chitinase and glucanase, more particularly β-1,3-glucanase, β-1,6-glucanase and chitinase. Preferably, the enzymes are applied together in a mixture because walls of fungal cells are normally constituted both of chitin and of glucan, in variable ratios.

Although mixtures of these cell wall lytic enzymes have shown to be effective against fungi, for preserving consumer products large scale use is still limited on account of the high cost price and their relatively low activity. A wider application could be envisaged, as soon as the effective dose and consequently the costs could be reduced.

For agrochemical compositions synergistic mixtures of the enzymes with non-food grade chemical fungicides are known (WO 90/03732 and Microbiology, 1994, 140, 623–629). A fully natural fungal growth inhibiting composition based on cell wall lytic enzymes is badly needed.

STATEMENT OF INVENTION

Microbial cell membrane affecting substances (MMAS) of natural origin have been found to inhibit fungal growth in synergistic admixture with at least one fungal cell wall lytic enzyme. The invention comprises compositions suitable for combatting fungi characterised in that it comprises at least one fungal cell wall lytic enzyme and at least one natural microbial membrane affecting substance in an effective concentration. Such substance is chosen preferably from the group consisting of nisin, amphiphilic alpha-helix forming peptides and fungal inhibitors which are present in herbs used for food preparation.

DETAILS OF THE INVENTION

Preferably, the cell wall lytic enzyme is chitinase or a glucanase or, more preferably, a mixture of them. The preferred glucanase is β-1,3-glucanase, optionally admixed with β-1,6-glucanase. The enzyme(s) can be used according to the invention as a separate, more or less pure enzyme isolate, but combinations of the enzymes are preferred. Crude preparations from natural origin containing the enzymes are commercially available and can be used instead of purified enzymes. One such enzyme preparation is marketed as NovoZyme™ 234, ex NOVO, Denmark, which is a mixture of lytic enzymes containing inter alia chitinase as well as β-1,3-glucanase and small amounts of β-1,6-glucanase. Such preparation is produced by fermentation of the fungus *Trichoderma harzianum* according to U.S. Pat. No. 4,353,891. Its use has been described in WO 90/03732. Other natural mixtures of chitinase and said glucanases can be obtained from vegetable sources, particularly from plants which are able to produce glucanase and chitinase as described in e.g. Plant Physiology 101: pp 857–863.

Chitinase as well as glucanase are preferably used in a concentration of 0.001–2 wt. % calculated on the composition. The amount of MMAS suitably is 0.00001–0.1 wt. %, preferably 0.0001–0.02 wt. % calculated on the composition. The preferred ratio of chitinase and β-1,3-glucanase is 1:9 to 9:1. Concentrations and ratio may be easily optimized depending on the actual composition ingredients. Antifungal compositions which are meant to be incorporated in products, contain the active ingredients in an increased concentration taking into account the dilution resulting from mixing.

The term natural refers to the origin of the substance. It means that the substance can be obtained from a natural source, even when the MMAS also could be obtained by synthetic preparation. Therefore the fungi combatting composition of the invention comprises MMAS irrespective of its way of preparation.

Several MMAS may be already known as such on account of their interference with cell membrane of microorganisms. Their action leads to disintegration or perforation of the cell membrane with fatal consequences for the microorganism. When used singly with intact fungi, the cell wall may form such hurdle that their fungi inhibiting properties were not or hardly perceived.

A well known natural MMAS to be used in the invention is the food-grade 3.5 kDa peptide nisin. Nisin being a bacteriocin has bactericidal activity, but no fungal growth inhibition has been observed (see FIG. 1).

To the known natural MMAS also belong peptides selected from the well known class of alpha-helix forming peptides. Alpha-helix forming peptides are suitable for use in the invention provided they have an amphiphilic character. This means that their three-dimensional peptide structure contains distinct regions with a hydrophobic character as well as distinct regions with a hydrophilic character. Amphiphilic alpha-helix forming peptides have a high isoelectric point and consequently carry a positive charge at a pH usually found in food products. This is an advantage, since the peptide's target are fungi cells wich carry an opposite charge at their outside.

A well known representative of the alpha-helix forming amphiphilic peptides is histatin. The name histatin in this respect denotes all known histatin peptides including histatin-1, histatin-3 and histatin-5 as well as mixtures of them. Their amino acid sequences are known. Histatin can be obtained by isolation from saliva as described in e.g. JP 04/182420, but a more practical way is to have it produced by a culture of a micro-organism provided with genes which code for the peptide.

Figure 4:
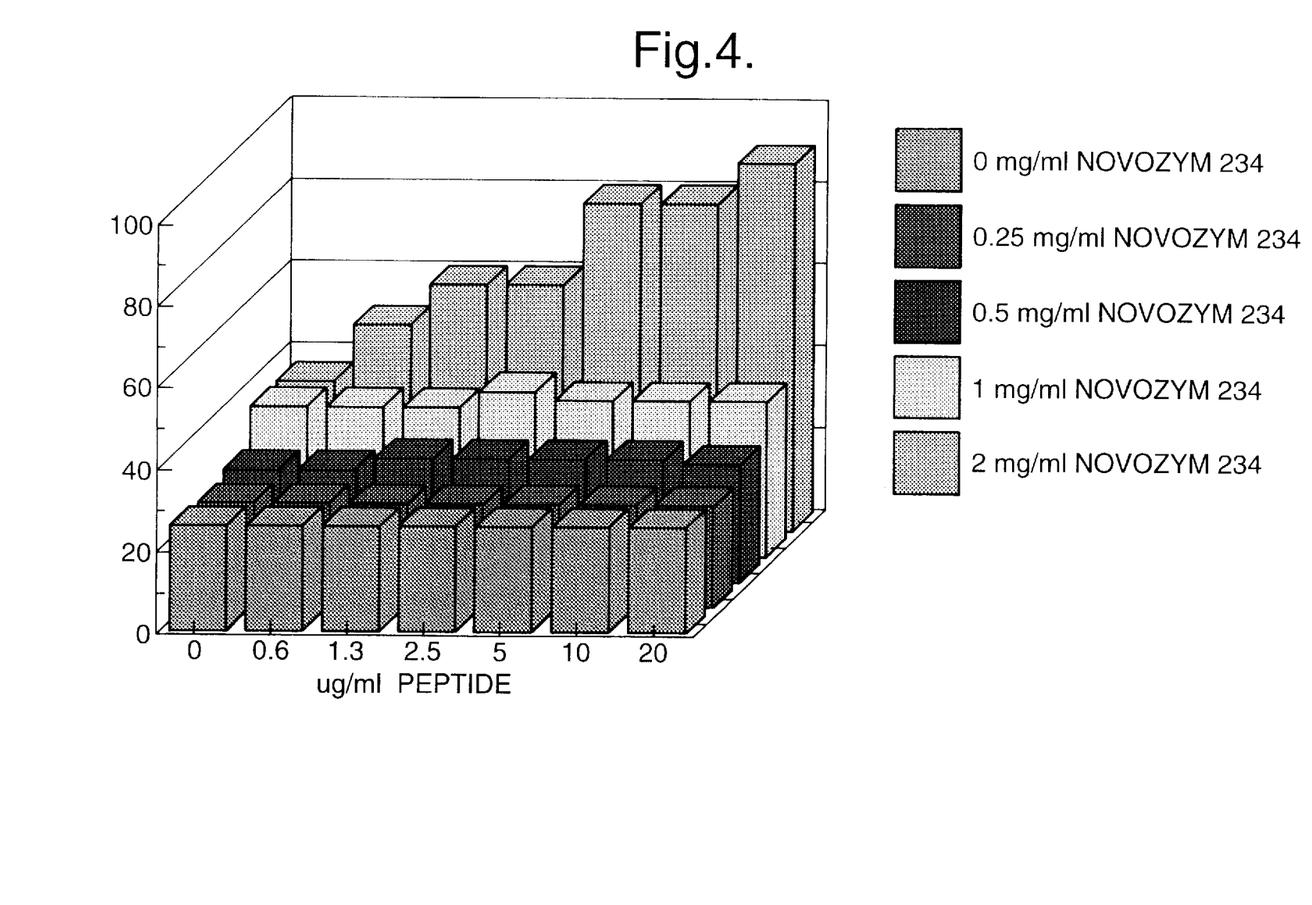
FIG. 4 shows the inhibition of outgrowth of *Saccharomyces cerevisiae* inoculated in malt extract broth in the presence of increasing amounts of cell wall lytic enzyme, and in the presence of increasing amounts of the polypeptide FASLLGKALKALAKQ (SEQ ID NO. 1).

Another membrane affecting alpha-helix forming amphiphilic peptide is the polypeptide FASLLGKALKA-LAKQ (SEQ ID NO: 1), where F=phenylalanine, A=alanine, S=serine, L=leucine, G=glycine, K=lysine, Q=glutamine. The polypeptide can be obtained synthetically by standard methods for peptide synthesis, but is preferably obtained by culturing a microorganism provided with the corresponding genetic code. Its synergistic activity with cell wall lytic enzymes is shown in FIG. 4. The first row shows the time for outgrowth of *Saccharomyces cerevisae* in the presence of varying amounts of the peptide. No effect of the peptide on growth is observed. The subsequent rows relate to outgrowth times with the same peptide concentrations but with increasing amounts of Novozyme™234. In the presence of 2 mg/ml of cell wall lytic enzyme, synergism is clearly visible.

Figure 5:
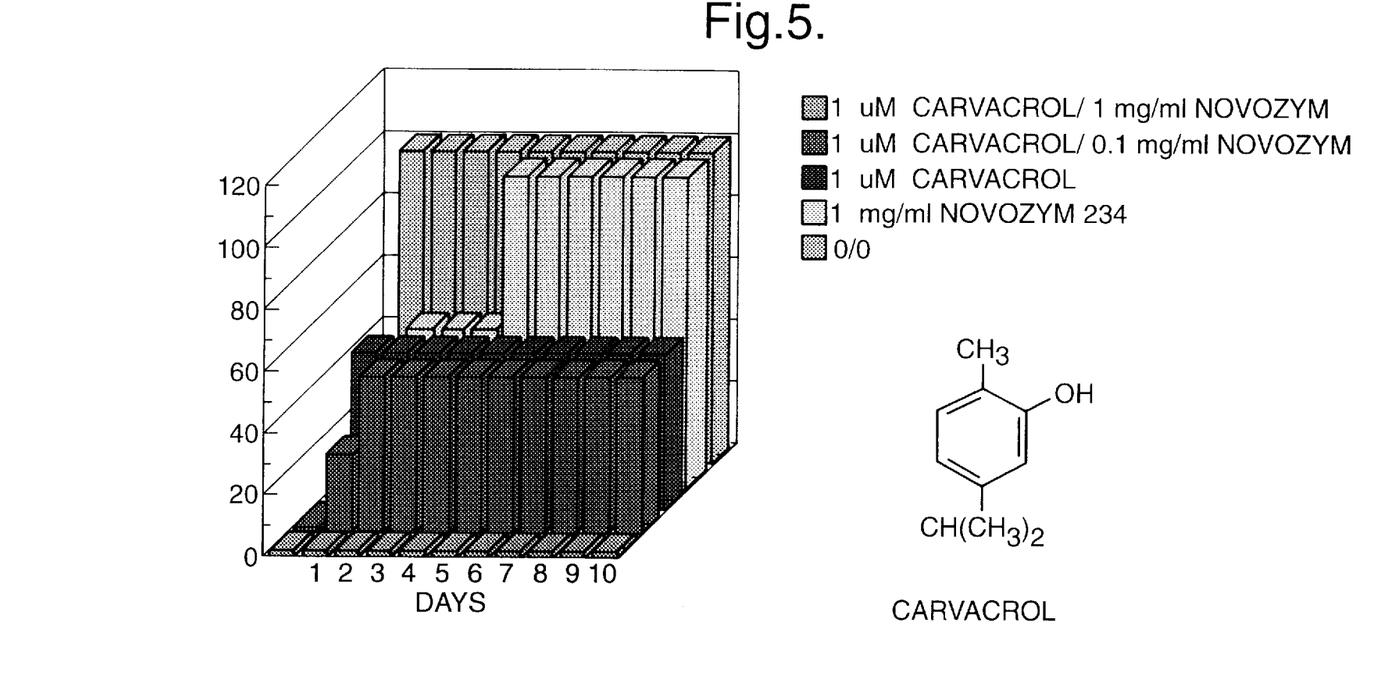
FIG. 5 shows the extent of outgrowth of *Paecilomyces variotii* inoculated in malt extract broth in the presence of cell wall lytic enzyme and/or in the presence of carvacrol.

Other natural MMAS acting as inhibitors of fungal growth are present in herbs which are suitable for food preparation, particularly for the preparation of cheese, such as chives, garlic and curcuma. Carvacrol, which molecular structure is shown in FIG. 5, exemplifies such inhibitors. Another suitable MMAS is sorbic acid which is known for anti-fungal use, but only when applied in high concentrations. Sorbic acid when used singly at the very low concentrations of the present invention does not show anti-fungal activity. For practical reasons the inhibiting compounds are preferably not isolated from the herbs, but applied in the form of the herbs in which they are contained. Preferably the herbs are used after a conditioning treatment, such as drying. Preferably the herbs are added in substantially dry form in a concentration of 0.01–10 wt. %.

The invention comprises too compositions where the MMAS is obtained by isolation from other materials including preparation by a synthetic process.

The synergistic activity of the combination comprising lytic enzyme and MMAS may vary, but generally is at least twice the activity of the same mixture in the absence of synergism of the constituting components. That means that for a desired activity only 50 wt. % or even less of the mixture is needed if it did not show synergistic activity. Synergy is clearly illustrated in each of FIGS. 1–7 appended to this specification.

Food compositions containing a fungal cell wall lytic enzyme and a MMAS benefit from the synergism first in that the costs for preservation are lowered because less preservative substance is needed. But, from a nutritional point of view even more important, is the reduction of the content of non-natural food additives. The preservation ingredients according to the invention are considered to be natural.

The invention comprises compositions to be used as preservation additives which contain both the lytic enzyme (s) and the MMAS as well as the ready consumer products in which these ingredients have been incorporated in proper amounts. For protection against airborne fungi the invention can take the form of dissolving the enzyme(s) and MMAS in an aqueous liquid and spraying the solution on the surface of a product which may be a food product, a cosmetic product or any other product which can be affected by fungal growth.

Beside the active ingredients the composition of the invention may contain auxiliary ingredients which are usual for fungi combatting compositions and which may include solid diluents, solvents, stabilizers and pH-regulators. The composition may be in the form of a powder, a paste or a liquid, depending on the envisaged way of application.

Although the composition of the invention is particularly suitable as a preservative for combatting fungi in food, it can be used as well for preventing or combatting undesired fungal growth on other products such as toiletries, e.g. soap bars. The cosmetic product may contain the fungi inhibitor not only for remaining itself fungi-free but also for the advantageous effect on the skin which is treated with such product, e.g. a shampoo being applied to a scalp with a fungal affliction. The invention is illustrated by the following examples.

EXAMPLE 1

Inhibition of fungal outgrowth with cell wall lytic enzyme and nisin.

An aqueous solution (demineralised water) was prepared containing 0.2 wt. % of the antifungal substance NovoZyme™ 234 and 0.002 wt. % of nisin. 75 µl of the solution were warmed to 20° C. and added to the well of a microtitre plate. Then 75 µl of a solution containing 4 wt. % of malt extract broth (ex Oxoid), 0.75 wt. % of agar (ex Difco) and 1000 spores of the fungus *Aspergillus niger* was heated to 25° C. and added to the test solution in the well (pH 5.1).

The procedure was repeated with solutions containing 0.004, 0.008, 0.016, 0.032 and 0.064 wt. % of nisin. The contents of the wells were thoroughly mixed and 75 µl of paraffin oil was loaded on top of the mixture. Finally, the plates were sealed with an oxygen permeable foil (Merlin).

During 360 hours the OD 620 nm was measured at regular intervals using a Multiscan devise MCC 340. Fungal outgrowth was defined when an OD (optical density) increase of at least 0.1 occurred.

Figure 1:
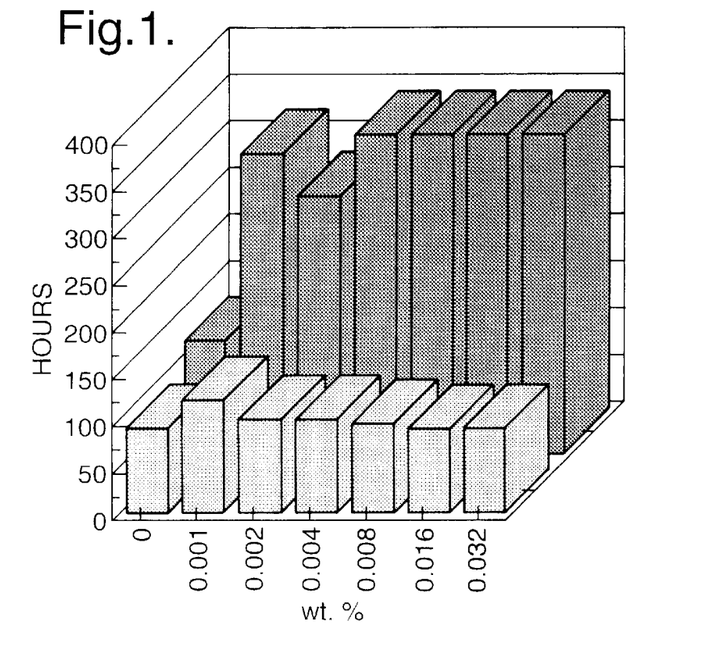
FIG. 1 shows inhibition of the outgrowth of the fungus *Aspergillus niger* as a function of nisin concentration with and without a cell wall lytic enzyme.

FIG. 1 shows the time (hours) needed for outgrowth of the spores of the fungus in an environment containing nisin in concentrations increasing from 0 to 0.032 wt. %. In the absence of any enzyme (first row) nisin itself has no substantial effect on postponing the onset of fungal growth beyond the 100 hours found for a nisin free mixture. The chitinase and glucanase containing enzyme preparation NovoZyme™ 234 (0.1 wt. %), when applied without nisin, does show hardly any fungal growth inhibition. However, mixtures containing nisin as well as the enzyme preparation (second row) show considerable activity, which is apparent from the strongly increased times needed for outgrowth.

EXAMPLE 2

Inhibition of fungal outgrowth with cell wall lytic enzyme and histatin.

An aqueous solution (demineralised water) was prepared containing 0.2 wt. % of the antifungal substance NovoZyme™ 234 and 0.002 wt. % of histatin. 75 µl of the solution were warmed to 20° C. and added to the well of a microtitre plate. Then 75 µl of a solution containing 4 wt. % malt extract broth (ex Oxoid), 0.75 wt. % agar (ex Difco) and 1000 spores of the fungus *Aspergillus niger* was heated to 25° C. and added to the test solution in the well (pH 5.1). The procedure was repeated with solutions containing 0.004, 0.008, 0.016, 0.032 and 0.064 wt. % of histatin. The contents of the wells were thoroughly mixed and 75 µl of paraffin oil was loaded on top of the mixture. Finally, the plates were sealed with an oxygen permeable foil (Merlin). During 360 hours the OD 620 nm was measured at regular intervals using a Multiscan devise MCC 340. Fungal outgrowth was defined when an OD increase of at least 0.1 occurred.

Figure 2:
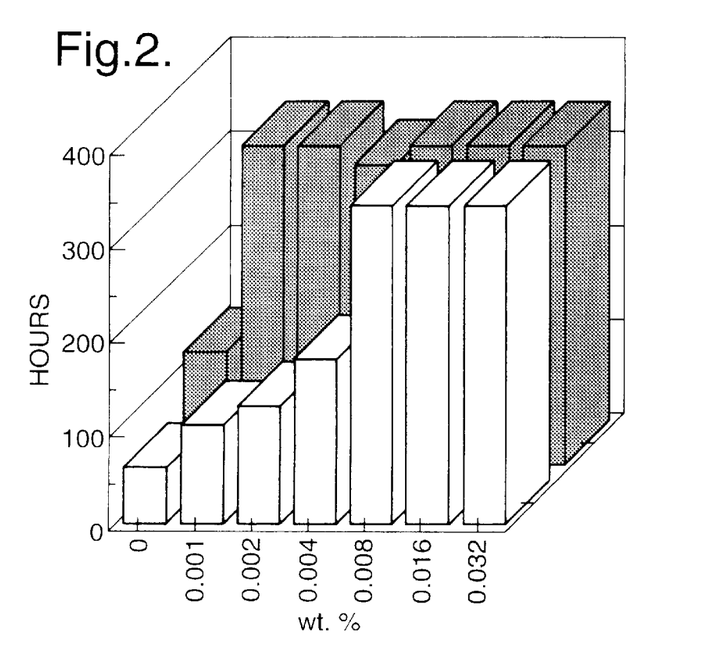
FIG. 2 shows inhibition of the outgrowth of the fungus *Aspergillus niger* as a function of histatin concentration with and without a cell wall lytic enzyme.

FIG. 2 shows the time (hours) needed for outgrowth of the spores of the fungus in an environment containing the peptide histatin in concentrations increasing from 0 to 0.032 wt. %. In the absence of any enzyme (first row) histatin appears to be slightly active in retarding fungal growth, particularly at a concentration of 0.008 wt. % and higher. The chitinase and glucanase containing enzyme preparation NovoZyme™ 234, when applied as such in a concentration of 0.1 wt. %, but without any histatin (second row, first bar) does show hardly any fungal growth inhibition. However, mixtures containing histatin as well as the enzyme preparation show considerable fungal growth inhibition even at histatin concentrations lower than 0.008 wt. % (second row).

EXAMPLE 3

Inhibition of fungal outgrowth with cell wall lytic enzyme and histatin.

Figure 3:
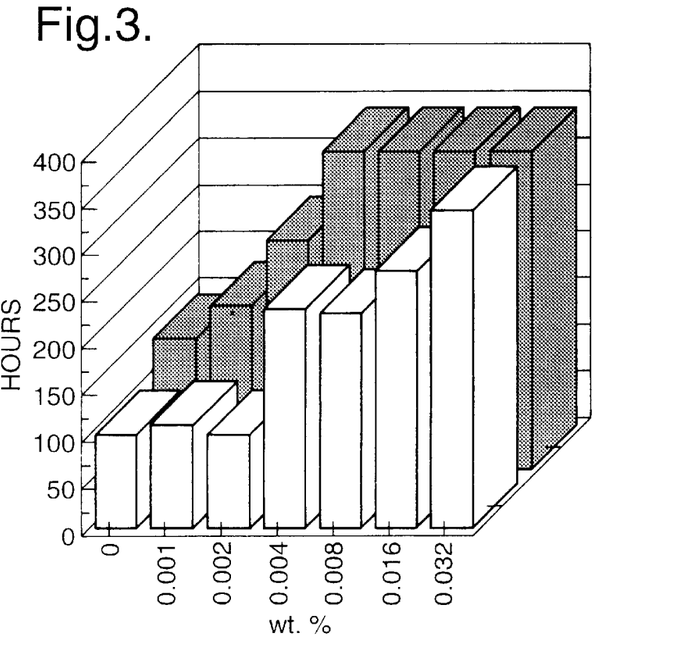
FIG. 3 shows inhibition of the outgrowth of the fungus *Paecilomyces variotii* as a function of histatin concentration with and without a cell wall lytic enzyme.

Example 2 is repeated with the fungus *Paecilomyces variotii*. Histatin without enzyme shows fungal growth inhibition at concentrations of 0.004 wt. % and higher (FIG. 3, first row). With the addition of 0.1 wt. % of enzyme mixture (second row) a clear raise in activity can be observed even at concentrations below 0.004 wt. % histatin.

EXAMPLE 4

Inhibition of fungal outgrowth with cell wall lytic enzyme and the polypeptide FASLLGKALKALAKQ (SEQ ID NO: 1)

An aqueous solution (demineralised water) was prepared containing 2 mg/ml of the antifungal preparation NovoZyme™ 234 and 40 µg/ml of the polypeptide. 75 µl of the solution were warmed to 20° C. and added to the well of a microtitre plate. Then 75 µl of a solution containing 4 wt. % of malt extract broth (ex Oxoid) and 1000 cells of the yeast *Saccharomyces cerevisiae* was heated to 25° C. and added to the test solution in the well (pH 5.1) yielding a mixture containing 20 µg/ml of the polypeptide.

The procedure was repeated yielding solutions each containing 2 mg/ml of Novozyme™ and 10, 5, 2.5, 1.3, 0.6 and 0 µg/ml respectively of polypeptide. A range of solutions with the same polypeptide concentrations was prepared but containing 1 mg/ml Novozyme™. Corresponding ranges were prepared containing 0.5, 0.25 and 0 mg/ml of Novozyme™.

The contents of the wells were thoroughly mixed and 75 µl of paraffin oil was loaded on top of the mixture. Finally, the plates were sealed with an oxygen permeable foil (Merlin). During 360 hours the OD 620 nm was measured at regular intervals using a Multiscan devise MCC 340. Fungal outgrowth was defined when an OD increase of at least 0.1 occurred.

FIG. 4 shows the time (hours) needed for outgrowth of the cells of the yeast in an environment containing the polypeptide and the enzyme in various concentrations. In the absence of any enzyme (first row) the polypeptide itself has no visible effect on fungal outgrowth. The preparation containing only NovoZyme™ 234 and no polypeptide, only shows some fungal growth inhibition in a concentration of at least 1 mg/ml lytic peptide. Synergism with the polypeptide is clearly visible at 2 mg/ml enzyme.

EXAMPLE 5

Inhibition of fungal outgrowth with cell wall lytic enzyme and carvacrol.

Solutions (30 ml) were prepared containing 1 µl carvacrol dissolved in malt extract broth. Novozyme™234 was present in concentrations of 1, 0.1 and 0 mg/ml. For comparison a solution was prepared containing 1 mg/ml of Novozyme™, but without carvacrol and one in which both enzyme and carvacrol were absent. 50 ml serum bottles filled with the solutions were inoculated with 1000 spores of *Paecilomyces variotii*. The height of the bars of FIG. 5 indicates the extent of outgrowth of the fungi observed during ten days. The highest bars ("100") indicate full outgrowth of the fungi, which occurs in solutions without carvacrol and with 1 mg/ml or less enzyme. Observed growth inhibition is expressed by the "50" bars. The presence of 1 µM carvacrol causes inhibition of growth, even in the absence of enzyme. When 1 mg/ml of enzyme is present together with 1 µM of carvacrol even germination of the fungal spores ("25" bars) does no longer occurs.

EXAMPLE 6

Inhibition of fungal outgrowth with cell wall lytic enzyme and herbs

In a laminar air flow cabinet homogeneous fresh-cheese samples were prepared containing 0, 0.5 and 2 wt. % of NovoZyme™ 234 powder and one containing 2 wt. % of inactivated NovoZyme™ 234 powder. The same series was prepared containing additionally 1.6 wt. % of a herbs mixture containing chives, garlic and curcuma. The products were filled into a small sterile lid (adhered into a bigger one) with a sterile knife such that a plain cheese surface was obtained.

A dry suspension of spores of *Penicillium roqueforti* was prepared and the number of fungi spores in the mixture was determined by spraying in 10 identical Malt Extract Agar samples in 10 jar lids. To prevent drying out these lids were screwed on a glass jar containing NaCl agar (aw=0.99). The jars were incubated for 3–5 days at 25° C. After incubation colonies were counted and the arithmetic average was taken to determine the number of fungi spores.

In the same way the cheese surfaces were inoculated with the same spores suspension. An inoculum resulted with 10(exp2) to 10(exp4) spores. The samples were screwed on a glass jar containing NaCl agar (aw=0.99) to avoid drying out and were incubated at 20° C.

During several weeks after inoculation the inoculated cheese samples were checked 3 times a week for visible fungi spoilage. Also the β-glucanase activity was measured for assessing the effect of storage time on enzyme activity in a cheese environment. No decrease of β-glucanase activity was found during the experiment. Table I shows the delay of fungal outgrowth for various compositions.

TABLE I

| Fungi growth at 20° C. on cheese | Visible fungi spoilage after n days |
|---|---|
| No preservation agent | 5 |
| Herbs only present (1.6 wt. %) | 7–10 |
| NovoZyme ™ 234 present (2 wt. %) | 7 |
| Herbs (1.6 wt. %) + NovoZyme ™ 234 (2 wt. %) present | >70 |

Figure 6:
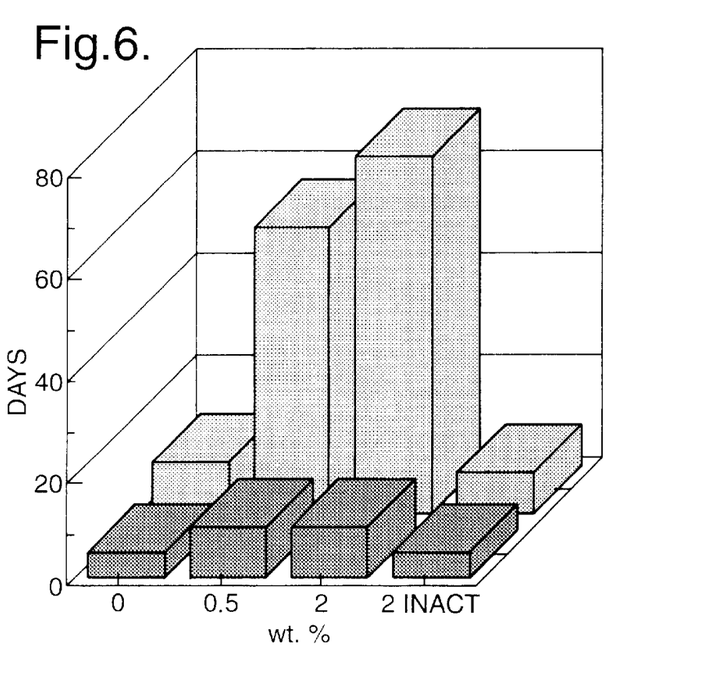
FIG. 6 shows the inhibition of the outgrowth of *Penicillium roqueforti* on a fresh cheese as a function of a cell wall lytic enzyme with and without admixed herbs.

FIG. 6, illustrating Table I, shows that the presence of both herbs and the NovoZyme™ 234 cocktail (second row) has a surprisingly strong synergistic inhibitory effect on the outgrowth of the *Penicillium roqueforti* fungi spores.

EXAMPLE 7

Food protected against fungal growth

The surface of processed cheese was inoculated in the centre with *Penicillium roqueforti*. Admixture of nisin of the lytic enzymes was done in a laminar air flow cabinet. The samples were observed during 16 days (see FIG. 7).

Figure 7:
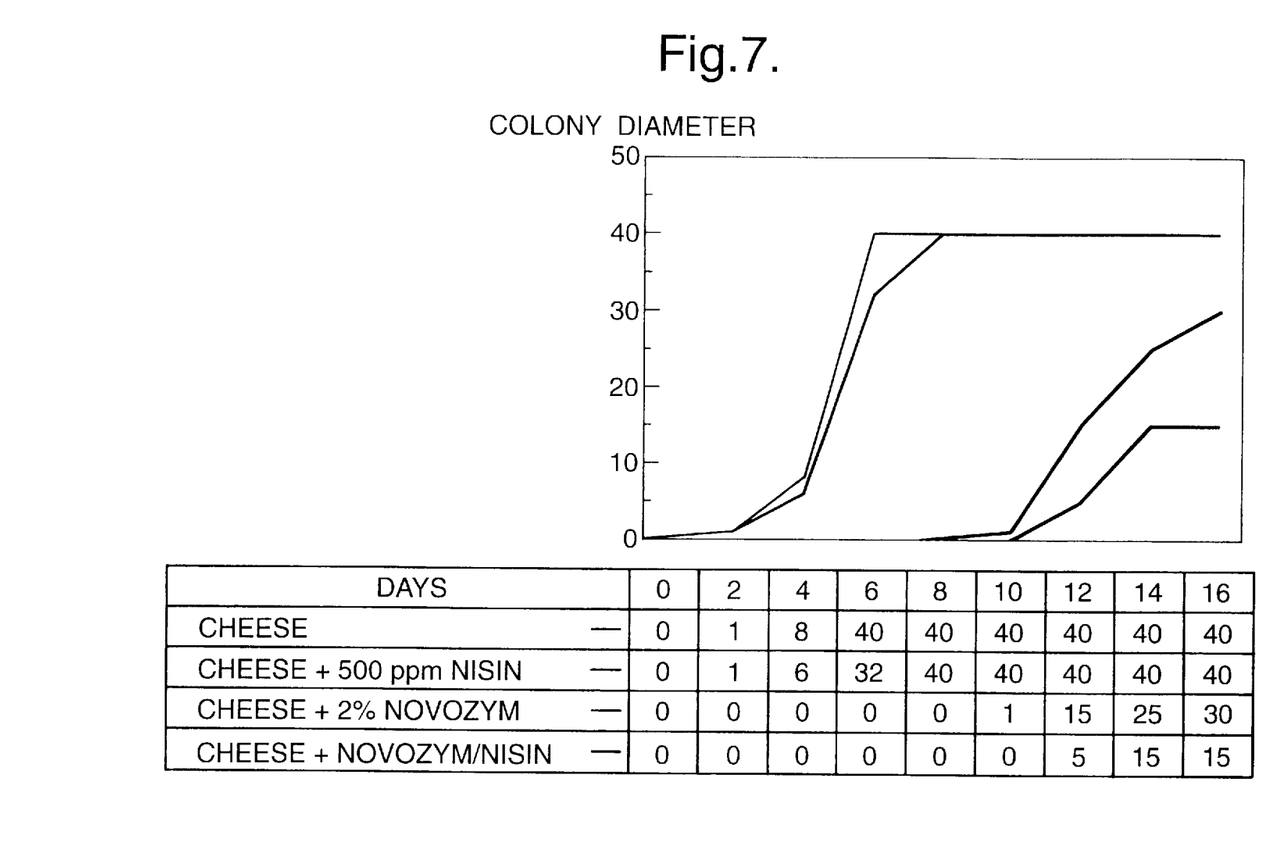
FIG. 7 shows the outgrowth of *Penicillium roqueforti* inoculated in processed cheese, during 16 days in the presence of only nisin, of only cell wall lytic enzyme, of both cell wall lytic enzyme and nisin and in the absence of both.
Figure 8:
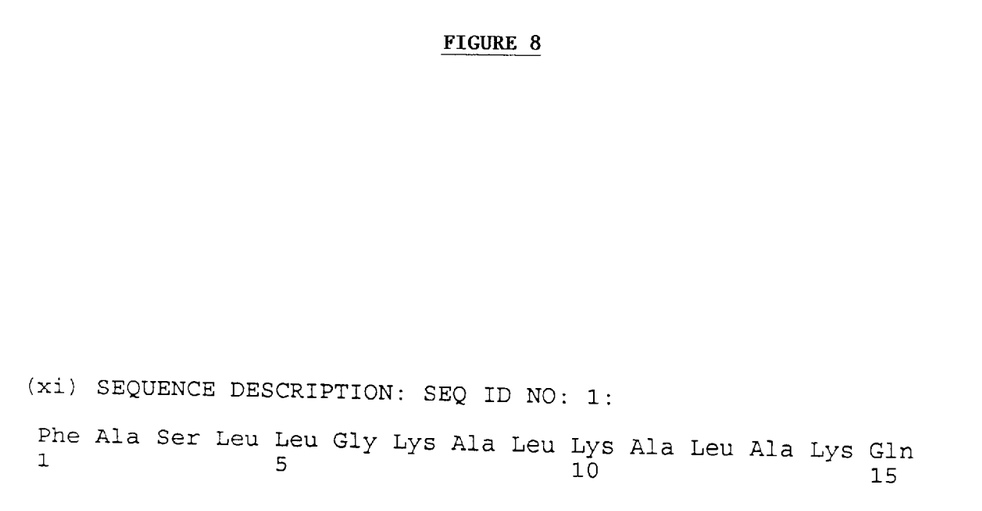
FIG. 8 shows the results of amino acid sequence for (SEQ ID NO: 1).

The sample containing no preservative at all or only 0.05 wt. % (500 ppm) of nisin showed fungal outgrowth already after 4 days. Fungal growth is expressed as the diameter of the colonies. When NovoZyme™ 234 (2 wt. %) was present fungal outgrowth was considerably delayed and became visible only after 12 days. But the sample which contained both NovoZyme™ (2 wt. %) and nisin (0.05 wt. %) showed considerably reduced outgrowth, even after 16 days.

We claim:

1. Composition suitable for combating fungi comprising at least one fungal cell wall lytic enzyme and at least one natural microbial membrane affecting substance (MMA) in an effective concentration selected from the group consisting of nisin, chives, garlic and curcuma.

2. Composition according to claim 1, characterized in that the composition contains chitinase as well as β-1,3-glucanase and, optionally β-1,6-glucanase.

3. Composition according to claim 2, characterized in that the ratio of chitinase and glucanase is 9:1 to 1:9.

4. Composition according to claim 2, characterized in that each of the enzymes chitinase and glucanase is present in a concentration of 0.001–2 wt. % calculated on the composition.

5. Composition according to claim 1, characterized in that the MMAS is present in a concentration of 0.00001–0.1 wt. %, calculated on the composition.

6. Composition according to claim 1 wherein the MMAS is present in a concentration of 0.0001–0.02 wt. %.

7. Composition according to claim 1, characterized in that the composition has a fungal growth inhibition activity which is at least twice the activity of the same mixture in the absence of synergism of the constituting components.

8. Composition according to claim 1, characterized in that the composition is a food product or a cosmetic preparation.

* * * * *